United States Patent [19]
Wester

[11] Patent Number: 5,651,374
[45] Date of Patent: Jul. 29, 1997

[54] COMBINATION PACKAGE AND APPLICATOR FOR CONDOM AND METHOD

[76] Inventor: Bryan K. Wester, 10441 Mahogany Key Cir. Apartment #104, Miami, Fla. 33196

[21] Appl. No.: 705,329

[22] Filed: Aug. 29, 1996

[51] Int. Cl.$^6$ ........................................................ A61F 6/04
[52] U.S. Cl. ........................................... 128/844; 128/918
[58] Field of Search ................................. 128/842, 844, 128/918; 604/647–353

[56] References Cited

U.S. PATENT DOCUMENTS

| | | | |
|---|---|---|---|
| 4,972,850 | 11/1990 | Broad | 128/844 |
| 4,987,905 | 1/1991 | Broad | 128/844 |
| 5,318,551 | 6/1994 | Di Cristo | 128/844 |
| 5,437,286 | 8/1995 | Stratton | 128/844 |
| 5,551,612 | 9/1996 | Hochfeld | 128/844 |

*Primary Examiner*—Michael A. Brown
*Attorney, Agent, or Firm*—Robert J. Van Der Wall

[57] ABSTRACT

A combination package and applicator condom assembly includes a condom having a condom tubular side wall, a condom end wall and a condom tubular side wall rim; and an assembly having a collar panel having a condom mounting port with a mounting port edge, the collar panel also having upper and lower radial tear lines extending generally outward from the mounting port edge respectively to the collar panel upper and lower edges; where the condom port edge and the condom side wall rim are interconnected and a circumferential tear line extends generally along the mounting port edge; and at least one pull tab panel pivotally connected to one collar panel edge, so that the at least one pull tab panel has a pull tab panel connected end and a pull tab panel free end for gripping and pulling by the user to apply tension to the collar panel to tear the collar panel along the radial and circumferential tear lines. A method is provided of applying the condom to a penis including the steps of deploying the condom; pivoting the at least one pull tab panel outwardly from the collar panel front face; gripping the at least one pull tab panel in a user hand; pulling the condom over the penis; and pulling the at least one pull tab panel laterally away from the collar panel so that the collar panel tears along the tear lines and thereby frees the assembly from the condom.

8 Claims, 4 Drawing Sheets

COMBINATION PACKAGE AND APPLICATOR FOR CONDOM AND METHOD

BACKGROUND OF THE INVENTION

1. Field of the Invention

The present invention relates generally to the field of birth control devices. More specifically the present invention relates to a combination package and applicator assembly for a condom. The condom is of conventional collapsed (not rolled) design, having a condom tubular side wall, a closed end with an end wall and an open end with a side wall rim. The inventive assembly is formed of several panels pivotally joined together at certain common edges. The assembly closes to become a condom package and opens to become a condom applicator.

The assembly includes a collar panel having a centrally located condom mounting port with a mounting port edge and with a port diameter substantially equivalent to the diameter of the condom tubular side wall. The collar panel also includes a collar panel upper edge, a collar panel lower edge, a collar panel first side edge and a collar panel second side edge, a collar panel front face and a collar panel rear face. Upper and lower radial perforation lines extend outwardly from the condom port edge to the collar panel upper and lower edges, respectively. The condom port edge and the condom side wall rim are interconnected to form a condom mounting joint, and a circumferential perforation line extends along the mounting port edge. First and second pull tab panels are pivotally connected to the collar panel first and second edges, respectively, so that each pull tab panel has a connected end and a free end. The first and second pull tab panels preferably taper toward their free ends.

A first cover panel is pivotally connected along the intersection between the first pull tab panel and the collar panel first side edge, and extends from the collar panel rear face. A second cover panel is optionally provided, and is pivotally connected along the intersection between the second pull tab panel and the collar panel second side edge and extends from the collar panel rear face. The assembly folds into a closed mode and into an open mode.

The assembly is initially provided in its closed mode, in which the condom is collapsed against the rear face of the collar panel. The first cover panel is folded over and against the condom, and the optional second cover panel is folded over and against the first cover panel. The first pull tab panel is folded over and against the collar panel front face, and the second pull tab panel is folded over and against the first pull tab panel. A light adhesive removably secures the second cover panel to the first cover panel and removably secures the second pull tab panel to the first pull tab panel.

To place the assembly in its open mode, the second cover panel is peeled off and separated from the first cover panel and pivoted outwardly from the collar panel. The first cover panel is pivoted off the condom and outwardly from the collar panel. The condom is deployed. The second pull tab panel is peeled off and separated from the first pull tab panel and pivoted outwardly from the collar panel front face to become substantially co-planar with the collar panel. The first pull tab panel is pivoted outwardly from the collar panel first face to become substantially co-planar with the collar panel. Then the first pull tab panel is gripped in the user left hand and the second pull tab panel is gripped in the user right hand and the collar panel front face is directed toward the penis. The user aligns the mounting port with the head of the penis and pulls the condom side wall rim over the penis, so that the condom is fully fitted. The first and second pull tab panels are then pulled to pull the condom fully over the penis. Then the first and second pull tab panels are thus pulled laterally away from each other so that the collar panel tears along the radial and circumferential perforations. This tearing frees the assembly away from the condom, so that only the condom remains in place on the penis.

2. Description of the Prior Art

There have long been various types of packages for condoms. These have included sealed envelopes, wrappers and flat metal containers. A problem with these packages has been that they form a barrier to rapid condom access. Another problem has been that they do not assist the user in condom application.

It is thus an object of the present invention to provide a combination package and applicator assembly for a condom.

It is another object of the present invention to provide such an assembly which holds the condom end open and which unwraps to present tabs for the user to grip for quickly and evenly pulling the condom over the penis.

It is still another object of the present invention to provide such an assembly which may be quickly torn away from the condom after the condom is in place.

It is finally an object of the present invention to provide such an assembly which is easy to use, reliable, compact and inexpensive to manufacture.

SUMMARY OF THE INVENTION

The present invention accomplishes the above-stated objectives, as well as others, as may be determined by a fair reading and interpretation of the entire specification.

A combination package and applicator condom assembly is provided including a condom having a condom tubular side wall with a condom tubular side wall diameter, a closed end with a condom end wall and an open end with a condom tubular side wall rim; a collar panel having a condom mounting port with a mounting port edge, the collar panel also having a collar panel upper edge and a collar panel lower edge, a collar panel first side edge and a collar panel second side edge, a collar panel front face and a collar panel rear face, upper and lower radial tear lines extending generally outward from the mounting port edge respectively to the collar panel upper and lower edges; where the condom port edge and the condom tubular side wall rim are interconnected to form a condom mounting joint, and a circumferential tear line extends generally along the mounting port edge; and at least one pull tab panel pivotally connected to one collar panel edge, so that the at least one pull tab panel has a pull tab panel connected end and a pull tab panel free end for gripping and pulling by the user to apply tension to the collar panel to tear the collar panel along the radial and circumferential tear lines.

The at least one pull tab panel preferably includes first and second pull tab panels extending from the collar panel first and second side edges respectively for simultaneous gripping and pulling by the user. The assembly preferably additionally includes a first cover panel pivotally connected to the collar panel first side edge and extending outwardly from the collar panel rear face, for protectively covering the condom until the condom is used. The assembly preferably additionally includes a second cover panel pivotally connected to the collar panel second side edge and extending outwardly from the collar panel rear face, for protectively covering the condom until the condom is used. The first and second pull tab panels preferably taper toward each pull tab panel free end. The mounting port is preferably substantially circular and has a diameter substantially equal to the condom tubular side wall diameter.

A method is provided of closing the above-described combination package and applicator condom assembly, including the steps of collapsing the condom against the collar panel rear face; folding the at least one cover panel over and against the condom; and folding the at least one pull tab panel over and against the collar panel front face.

A method is also provided of applying a condom to a penis using the above-described combination package and applicator condom assembly, including the steps of deploying the condom; pivoting the at least one pull tab panel outwardly from the collar panel front face; gripping the at least one pull tab panel in a user hand; directing the collar panel front face toward the penis; aligning the mounting port with the head of the penis and pulling the condom tubular side wall rim over the penis; pulling the at least one pull tab panel laterally away from the collar panel so that the collar panel tears along the radial and circumferential tear lines, thereby freeing the condom from the assembly so that the condom remains in place on the penis.

BRIEF DESCRIPTION OF THE DRAWINGS

Various other objects, advantages, and features of the invention will become apparent to those skilled in the art from the following discussion taken in conjunction with the following drawings, in which.

DETAILED DESCRIPTION OF THE PREFERRED EMBODIMENTS

Figure 1:
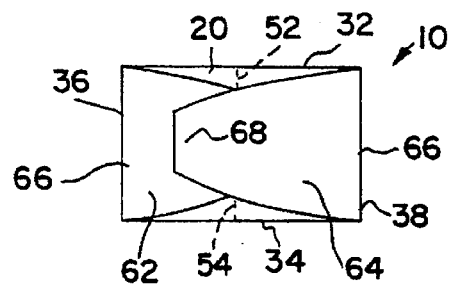
FIG. 1 is a front view of the assembly in the folded, closed mode in which a user would purchase the assembly.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings, wherein like characteristics and features of the present invention shown in the various FIGURES are designated by the same reference numerals.

Preferred Embodiment

Figure 2:
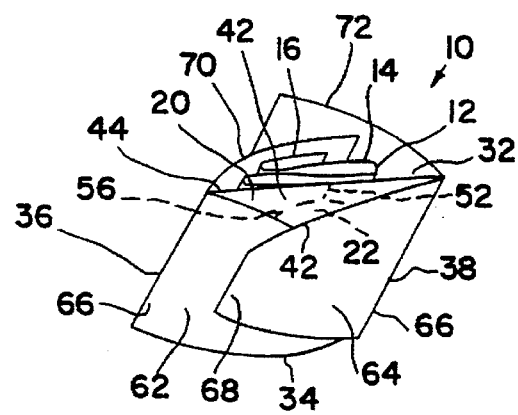
FIG. 2 is a perspective view of the assembly, partly opened.
Figure 3:
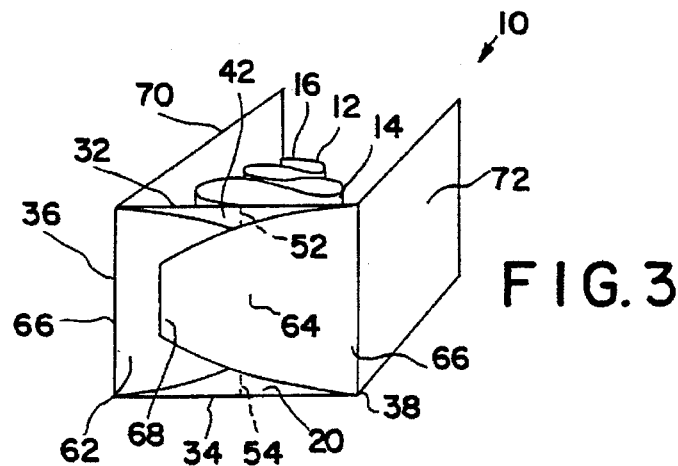
FIG. 3 is a perspective view of the assembly of FIG. 2 with both cover panels opened.
Figure 4:
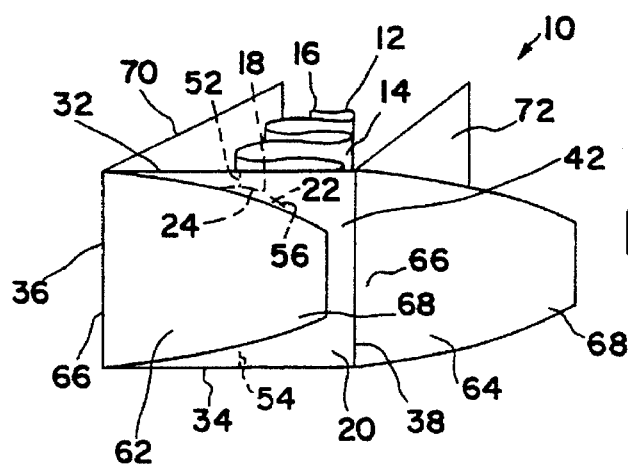
FIG. 4 is a perspective view of the assembly of FIG. 3 with the outer, second pull tab panel opened.
Figure 5:
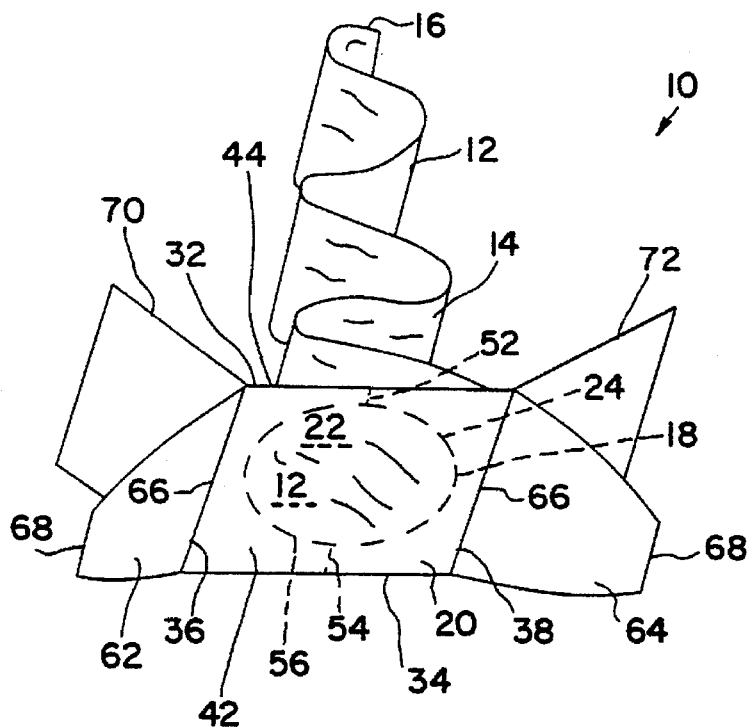
FIG. 5 is a perspective view of the assembly of FIG. 4 with both pull tab panels opened and the condom partly deployed.
Figure 6:
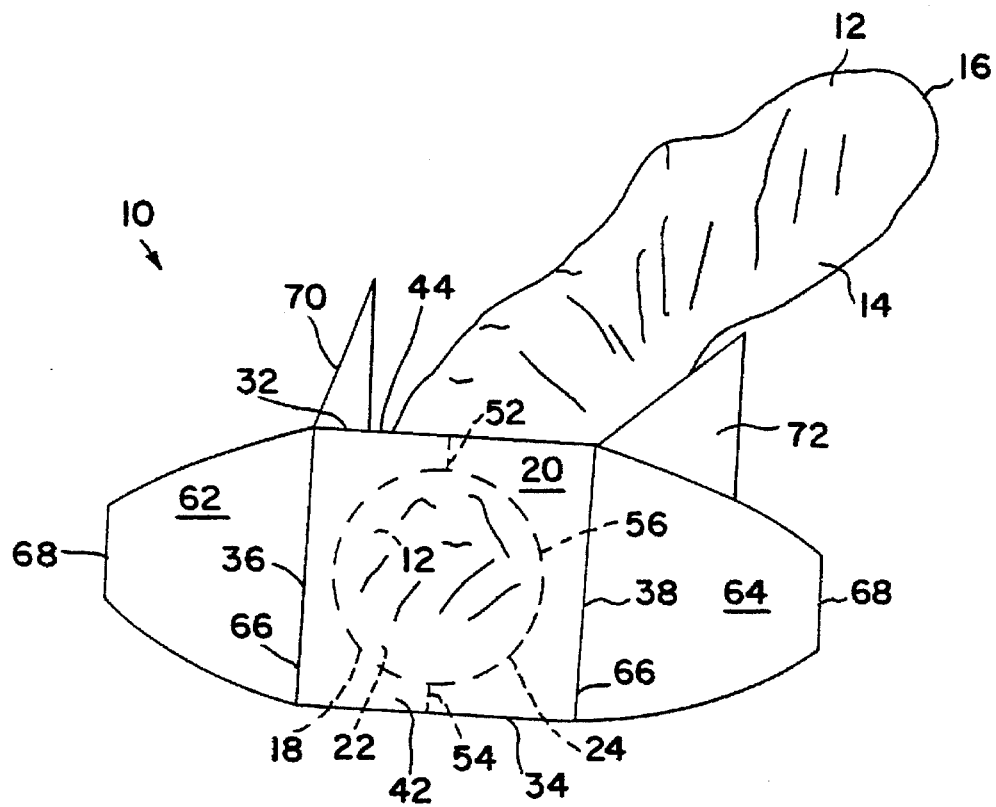
FIG. 6 is a perspective view as in FIG. 5 with the condom fully deployed and the apparatus ready for application to a penis.
Figure 7:
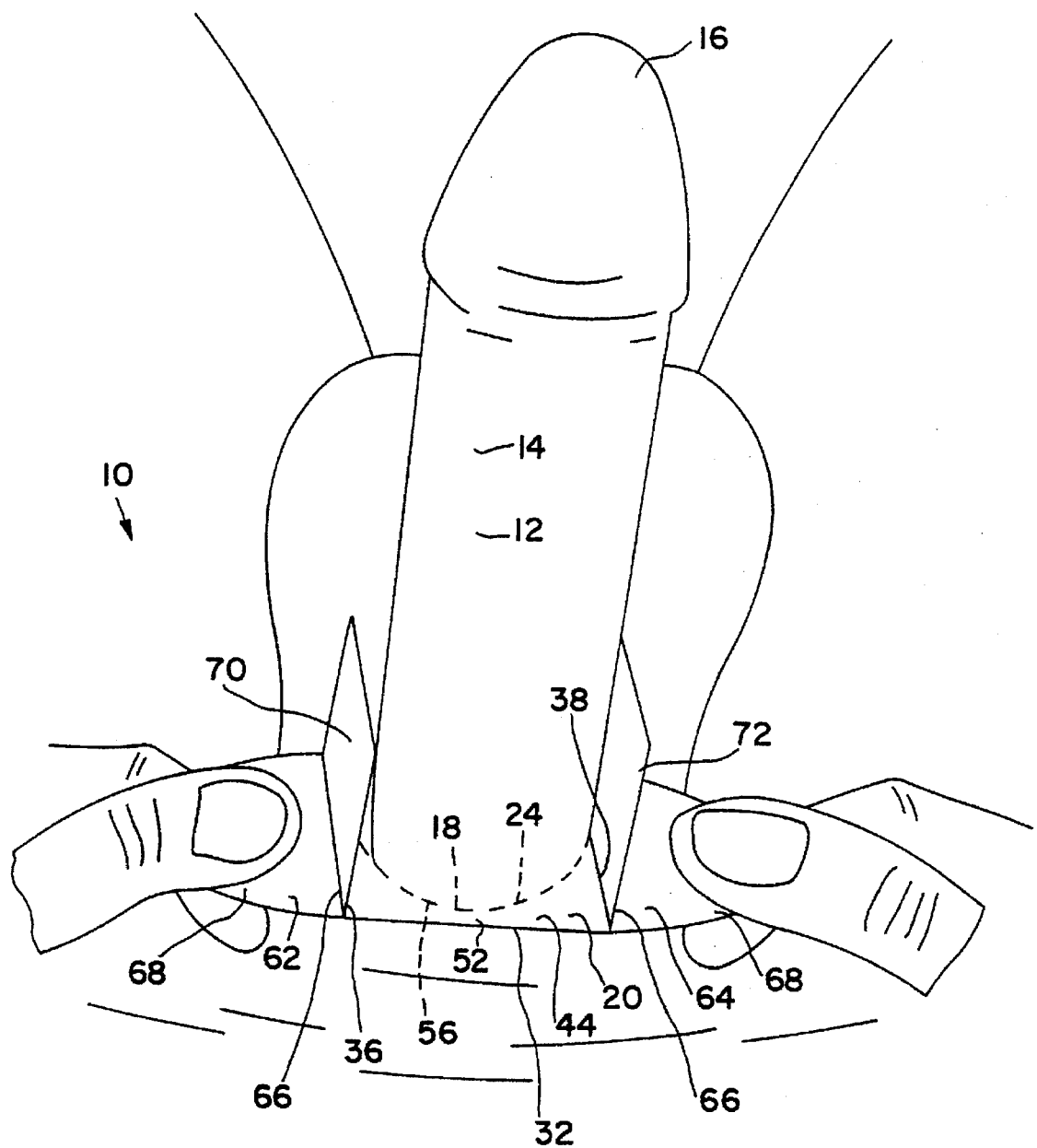
FIG. 7 is a perspective view of the apparatus being gripped by the pull tab panels and pulled toward the user so that the condom slides onto the penis.
Figure 8:
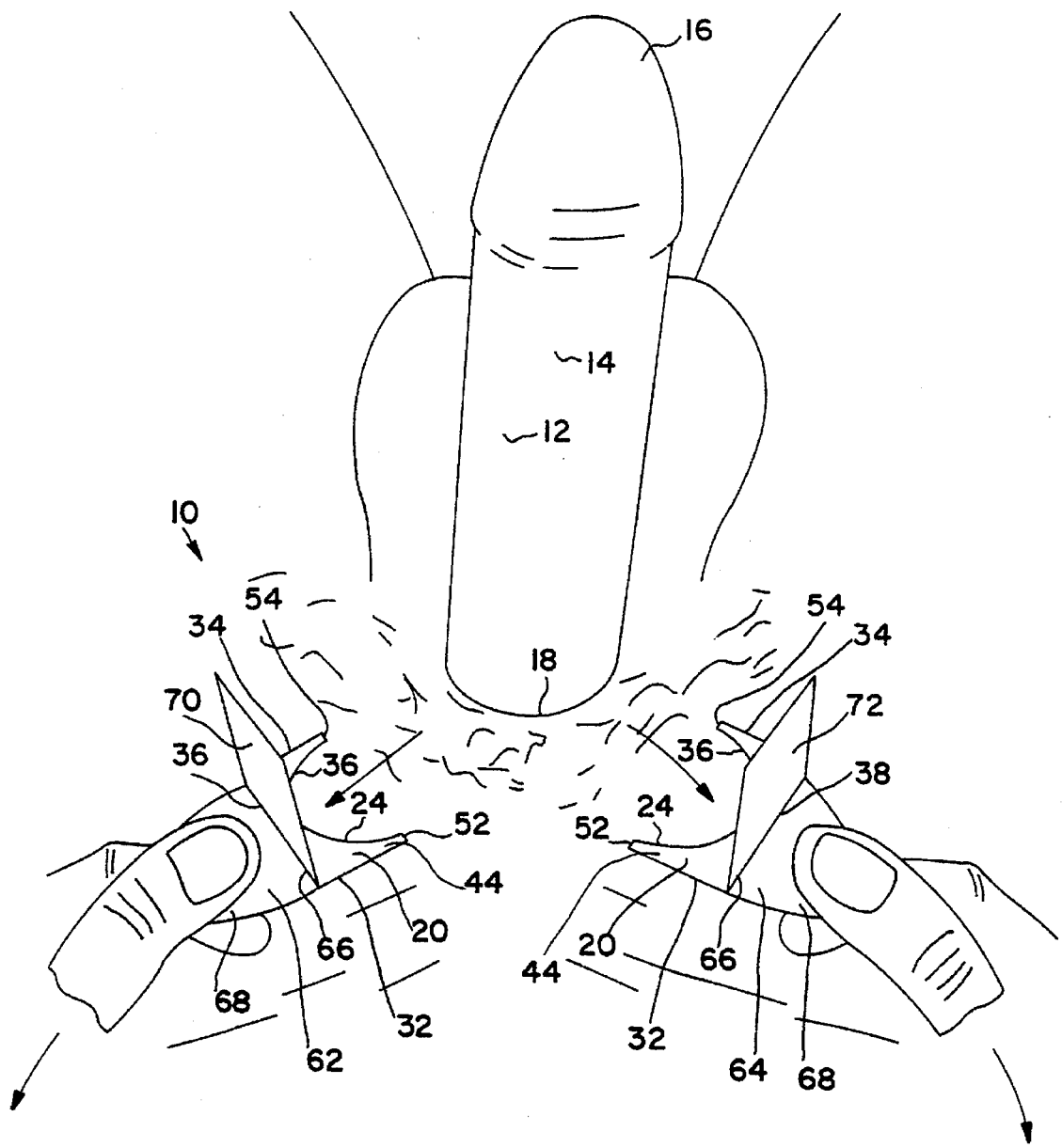
FIG. 8 is a perspective view as in FIG. 7, showing how the assembly is torn away from the condom along the radial and circumferential perforation lines after the condom is fully in place on the penis.

Referring to FIGS. 1–8, a combination package and applicator assembly 10 is disclosed for a condom 12. The condom 12 is of conventional design, having a condom tubular side wall 14, a closed end with a condom end wall 16 and an open end with a condom tubular side wall rim 18. Assembly 10 is formed of several panels pivotally joined together at certain common panel edges.

Assembly 10 includes a collar panel 20 having a centrally located circular condom mounting port 22 with a mounting port edge 24 and with a mounting port diameter substantially equivalent to the diameter of the condom tubular side wall 14. See FIGS. 1–4. Collar panel 20 also includes a collar panel upper edge 32 and a collar panel lower edge 34, a collar panel first side edge 36 and a collar panel second side edge 38, and a collar panel front face 42 and a collar panel rear face 44. Upper and lower radial perforation lines 52 and 54 extend outwardly from the mounting port edge 24 to collar panel upper and lower edges, 32 and 34, respectively. See FIGS. 5, 6 and 8. The mounting port edge 24 and the condom tubular side wall rim 18 are interconnected to form a condom mounting joint, which holds the condom open end in an open position for rapid condom application. A circumferential perforation line 56 extends along mounting port edge 24. It is understood that the above-referenced radial and circumferential perforation lines are simply preferred forms of tear lines which have the characteristic of tearing under collar panel 20 tension before other parts of collar panel 20 can tear.

First and second pull tab panels 62 and 64 are pivotally connected to collar panel first and second side edges 36 and 38, respectively, so that each pull tab panel 62 and 64 has a connected end 66 and a free end 68. First and second pull tab panels 62 and 64 preferably taper toward their free ends 68.

A first cover panel 70 is pivotally connected along the intersection between first pull tab panel 62 and collar panel first side edge 36, and extends from collar panel rear face 44. A second cover panel 72 is optionally provided, and is pivotally connected along the intersection between second pull tab panel 64 and collar panel second side edge 38 and extends from rear face 44. Assembly 10 folds into a closed mode and unfolds into an open mode.

Method

In practicing the invention, the following method may be used. Assembly 10 is provided to a user in its closed mode. See FIGS. 1 and 2. To place assembly 10 in its closed mode, condom 12 is collapsed against collar panel rear face 44. First cover panel 70 is folded over and against collapsed condom 12, and the optional second cover panel 72 is folded over and against first cover panel 70. First pull tab panel 62 is folded over and against collar panel front face 42, and second pull tab panel 64 is folded over and against first pull tab panel 62. A light adhesive removably secures second cover panel 72 to first cover panel 70 and removably secures second pull tab panel 64 to first pull tab panel 62.

To place assembly 10 in its open mode, second cover panel 72 is peeled off and separated from first cover panel 70 and then pivoted outwardly from collar panel rear face 44. First cover panel 70 is pivoted off condom 12 and outwardly from collar panel rear face 44. Condom 12 is then deployed. See FIGS. 3–6. Second pull tab panel 64 is peeled off and separated from first pull tab panel 62 and pivoted outwardly from collar panel front face 42 to become substantially co-planar with collar panel 20. First pull tab panel 62 is pivoted outwardly from collar panel front face 42 to become substantially co-planar with collar panel 20.

Then first pull tab panel 62 is gripped in the user left hand and second pull tab panel 64 is gripped in the user right hand, and collar panel front face 42 is directed toward the penis. The user aligns mounting port 22 with the head of the penis and pulls the condom tubular side wall rim 18 over the penis, so that the condom 12 is fully fitted onto the penis. See FIG. 7. Then the first and second pull tab panels 62 and 64 are pulled laterally away from each other so that collar panel 20 tears along radial perforation lines 52 and 54 and circumferential perforation line 56. See FIG. 8. This tearing entirely frees assembly 10 from condom 12, so that only condom 12 remains in place on the penis.

It is alternatively contemplated that cover panels 70 and 72 extend from collar panel upper and lower edges 32 and 34, respectively. Upper and lower radial perforation lines 52 and 54 respectively extend through cover panels 70 and 72 for this alternative version.

The various panels making up assembly 10 are preferably formed of cardboard or plastic. Alternatively, these panels may be formed of the same material making up the condom 12 itself.

While the invention has been described, disclosed, illustrated and shown in various terms or certain embodiments or modifications which it has assumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A combination package and applicator condom assembly, comprising:

a condom having a condom tubular side wall with a condom tubular side wall diameter, a closed end with a condom end wall and an open end with a condom tubular side wall rim;

a collar panel having a condom mounting port with a mounting port edge, said collar panel also having a collar panel upper edge and a collar panel lower edge, a collar panel first side edge and a collar panel second side edge, a collar panel front face and a collar panel rear face, upper and lower radial tear lines extending generally outward from said mounting port edge respectively to said collar panel upper and lower edges; wherein said condom port edge and said condom side wall rim are interconnected to form a condom mounting joint, and a circumferential tear line extends generally along said mounting port edge;

and at least one pull tab panel pivotally connected to one said collar panel edge, such that said at least one pull tab panel has a pull tab panel connected end and a pull tab panel free end for gripping and pulling by the user to apply tension to said collar panel to tear said collar panel along said radial and circumferential tear lines.

2. The assembly of claim 1, wherein said at least one pull tab panel comprises first and second pull tab panels extending from said collar panel first and second side edges respectively for simultaneous gripping and pulling by the user away from said condom.

3. The assembly of claim 1, additionally comprising:

a first cover panel pivotally connected to said collar panel first side edge and extending outwardly from said collar panel rear face, for protectively covering said condom until said condom is used.

4. The assembly of claim 3, additionally comprising:

a second cover panel pivotally connected to said collar panel second side edge and extending outwardly from said collar panel rear face, for protectively covering said condom until said condom is used.

5. The assembly of claim 2, wherein said first and second pull tab panels taper toward each said pull tab panel free end.

6. The assembly of claim 1, wherein said mounting port is substantially circular and has a diameter substantially equal to said condom tubular side wall diameter.

7. A method of closing a condom package and applicator assembly comprising a condom having a condom tubular side wall with a condom tubular side wall diameter, a closed end with a condom end wall and an open end with a condom side wall rim and comprising a package and applicator assembly having a collar panel having a condom mounting port with a mounting port edge, said collar panel also having a collar panel upper edge, a collar panel lower edge, a collar panel first side edge and a collar panel second side edge, a collar panel front face and a collar panel rear face, upper and lower radial tear lines extending generally outward from said mounting port edge respectively to said collar panel upper and lower edges; wherein said condom port edge and said condom side wall rim are interconnected to form a condom mounting joint, and a circumferential tear line extends generally to along said mounting port edge; and at least one pull tab panel pivotally connected to one said collar panel edge, such that said at least one pull tab panel has a pull tab panel connected end and a pull tab panel free end for gripping and pulling by the user to apply tension to said collar panel to tear said collar panel along said radial and circumferential tear lines, and a first cover panel pivotally connected to said collar panel first side edge and extending outwardly from said collar panel rear face, for protectively covering said condom until said condom is used; comprising the steps of:

collapsing said condom against said rear face of said collar panel;

folding said at least one cover panel over and against said condom;

and folding said at least one pull tab panel over and against the collar panel front face.

8. A method of applying a condom to a penis using condom package and applicator assembly comprising a condom having a condom tubular side wall with a condom tubular side wall diameter, a closed end with a condom end wall and an open end with a condom side wall rim and comprising a package and applicator assembly having a collar panel having a condom mounting port with a mounting port edge, said collar panel also having a collar panel upper edge, a collar panel lower edge, a collar panel first side edge and a collar panel second side edge, a collar panel front face and a collar panel rear face, upper and lower radial tear lines extending generally outward from said mounting port edge respectively to said collar panel upper and lower edges; wherein said condom port edge and said condom side wall rim are interconnected to form a condom mounting joint, and a circumferential tear line extends generally along said mounting port edge; and at least one pull tab panel pivotally connected to one said collar panel edge, such that said at least one pull tab panel has a pull tab panel connected end and a pull tab panel free end for gripping and pulling by the user to apply tension to said collar panel to tear said collar panel along said radial and circumferential tear lines, comprising the steps of:

deploying said condom;

pivoting said at least one pull tab panel outwardly from said collar panel front face;

gripping said at least one pull tab panel in a user hand;

directing said collar panel front face toward the penis;

aligning said mounting port with the head of the penis and pulling said condom side wall rim over the penis;

pulling said at least one pull tab panel laterally away from said collar panel such that said collar panel tears along said radial and circumferential tear lines, thereby freeing said condom from said assembly such that said condom remains in place on the penis.

* * * * *